United States Patent
Takano et al.

(10) Patent No.: US 9,700,629 B2
(45) Date of Patent: Jul. 11, 2017

(54) COMPOSITION CONTAINING S-ADENOSYL-L-METHIONINE WITH EXCELLENT STORAGE STABILITY

(75) Inventors: Kentaro Takano, Niigata (JP); Shinyo Gayama, Niigata (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 177 days.

(21) Appl. No.: 14/238,029

(22) PCT Filed: Jul. 20, 2012

(86) PCT No.: PCT/JP2012/068492
§ 371 (c)(1),
(2), (4) Date: Apr. 9, 2014

(87) PCT Pub. No.: WO2013/024663
PCT Pub. Date: Feb. 21, 2013

(65) Prior Publication Data
US 2014/0213542 A1    Jul. 31, 2014

(30) Foreign Application Priority Data

Aug. 12, 2011   (JP) .................. 2011-176921
Aug. 12, 2011   (JP) .................. 2011-176922

(51) Int. Cl.
| | | |
|---|---|---|
| *A61K 31/7076* | (2006.01) | |
| *A61K 47/38* | (2006.01) | |
| *A61K 47/42* | (2017.01) | |
| *A61K 47/36* | (2006.01) | |
| *A61K 9/14* | (2006.01) | |
| *A61K 9/16* | (2006.01) | |
| *A61K 9/19* | (2006.01) | |
| *C12P 19/40* | (2006.01) | |
| *A61K 36/064* | (2006.01) | |

(52) U.S. Cl.
CPC .............. *A61K 47/36* (2013.01); *A61K 9/146* (2013.01); *A61K 9/1652* (2013.01); *A61K 9/1658* (2013.01); *A61K 9/19* (2013.01); *A61K 31/7076* (2013.01); *A61K 36/064* (2013.01); *A61K 47/38* (2013.01); *A61K 47/42* (2013.01); *C12P 19/40* (2013.01)

(58) Field of Classification Search
CPC ........ A61K 9/146; A61K 9/19; A61K 9/1652; A61K 9/1658; A61K 47/36; A61K 47/38; A61K 47/42; A61K 36/064; A61K 31/7076
USPC ........................................................ 514/46
See application file for complete search history.

(56) References Cited

U.S. PATENT DOCUMENTS

| | | | | |
|---|---|---|---|---|
| 4,025,659 A | * | 5/1977 | Cho .................. | A23C 11/06 426/613 |
| 5,466,678 A | | 11/1995 | Kawabata et al. | |
| 6,028,208 A | * | 2/2000 | Gao .................. | C07C 401/00 552/653 |
| 7,026,361 B2 | * | 4/2006 | Minemura .............. | A61K 9/10 424/94.1 |
| 2003/0069202 A1 | * | 4/2003 | Kern .................. | A23C 9/13 514/46 |
| 2005/0272687 A1 | | 12/2005 | Hebert | |
| 2009/0088404 A1 | * | 4/2009 | Freedman ............ | A61K 9/2009 514/46 |
| 2010/0075403 A1 | | 3/2010 | Takano et al. | |
| 2010/0280064 A1 | | 11/2010 | Watanabe et al. | |
| 2011/0052623 A1 | | 3/2011 | Ueda et al. | |
| 2013/0028878 A1 | | 1/2013 | Takano et al. | |

FOREIGN PATENT DOCUMENTS

| | | | | |
|---|---|---|---|---|
| CN | 1483829 A | 3/2004 | | |
| JP | 11-322592 A | 11/1999 | | |
| JP | 2004-352669 A | 12/2004 | | |
| JP | 2005-229812 A | 9/2005 | | |
| JP | 2008-012464 A | 1/2008 | | |
| JP | 4479932 B2 | 6/2010 | | |
| KR | 10-2009-0112654 | 10/2009 | | |
| NZ | 526350 A | * 10/2004 | ........... | A61K 31/045 |
| WO | WO 2008/072532 A1 | 6/2008 | | |

(Continued)

OTHER PUBLICATIONS

AgResearch Magazine, 2008, 56(10), 1-3.*
International Search Report issued Sep. 4, 2012 in PCT/JP2012/068492.
F. Schlenk, et al., "The Formation of *S*-Adenosylmethionine in Yeast" The Journal of Biological Chemistry,1957, vol. 229, pp. 1037-1050.
Alessandra Morana, et al., "Stabilization of *S*-adenosyl-L-methionine promoted by trehalose" Biochemica et Biophysica Acta, vol. 1573, 2002, pp. 105-108.

(Continued)

*Primary Examiner* — Ganapathy Krishnan
(74) *Attorney, Agent, or Firm* — Oblon, McClelland, Maier & Neustadt, L.L.P.

(57) ABSTRACT

The present invention relates to a composition including S-adenosyl-L-methionine; and at least one kind of additive selected from carboxymethylcellulose, hydroxypropylcellulose, soybean polysaccharide, casein sodium, and zein, in which S-adenosyl-L-methionine is extracted from S-adenosyl-L-methionine-containing cells obtained by culturing a microorganism having an ability to produce SAMe, and the content of the additive in the composition falls within the range of 0.05 to 15 times by mass of S-adenosyl-L-methionine in the composition. The present invention provides a composition containing a high concentration of S-adenosyl-L-methionine, which is useful as a water-soluble physiologically active substance, and being excellent in storage stability and bioabsorbability. The present invention also relates to a molded article formed by using the composition and a method of producing the composition.

8 Claims, No Drawings

(56) References Cited

FOREIGN PATENT DOCUMENTS

| WO | WO 2008/090905 A1 | 7/2008 |
| WO | WO 2009/081833 A1 | 7/2009 |
| WO | WO 2010/089674 A1 | 8/2010 |
| WO | WO 2011/126030 A1 | 10/2011 |

OTHER PUBLICATIONS

Yong Wang, et al., "Simultaneous quantification of 11 pivotal metabolites in neural tube defects of HPLC-electrospray tandem mass spectrometry" Journal of Chromatography B, vol. 863, 2008, pp. 94-100.

* cited by examiner

COMPOSITION CONTAINING S-ADENOSYL-L-METHIONINE WITH EXCELLENT STORAGE STABILITY

CROSS REFERENCE TO RELATED APPLICATIONS

The present application is a 35 U.S.C. §371 national stage patent application of International patent application PCT/JP2012/068492, filed on Jul. 20, 2012, published as WO/2013/024663 on Feb. 21, 2013, the text of which is incorporated by reference, and claims the benefit of the filing date of Japanese application nos. 2011-176921, filed on Aug. 12, 2011, and 2011-176922, filed on Aug. 12, 2011, the text of both of which is also incorporated by reference.

TECHNICAL FIELD

The present invention relates to a composition containing a high concentration of S-adenosyl-L-methionine, which is useful as a water-soluble physiologically active substance, and being excellent in storage stability. The present invention also relates to a molded article formed by using the composition and a method of producing the composition.

BACKGROUND ART

S-adenosyl-L-methionine (hereinafter referred to as SAMe) occurs widely in living organisms. SAMe is a water-soluble physiologically active substance playing a key role as a methyl donor involved in the methylation by a wide range of transmethylase in the synthesis and metabolism of nucleic acid, neurotransmitter, phospholipid, hormone, protein, or the like. SAMe is observed in almost all human cells, serves as a cofactor in various biochemical reactions, and is metabolized through three metabolic pathways: transmethylation, transsulfuration, and transaminopropylation. For example, SAMe is an essential substance for the maintenance of cartilage and the biosynthesis of brain chemicals. A recent function study has reported that SAMe has a therapeutic effect on fatty liver, hyperlipemia, arteriosclerosis, insomnia, alcoholic hepatitis, senile dementia, and the like. As just described, SAMe is an important physiologically active substance and is widely used in Euramerican countries as a therapeutic agent for depression, liver disorder, arthritis, and the like or as a health food.

Therefore, it is strongly desired that SAMe be produced and supplied conveniently and inexpensively. Conventionally, the well-known methods of producing SAMe include a fermentation method of using a culture medium containing L-methionine as a precursor, an enzymatic synthesis method of allowing substrates: adenosine 5'-triphosphate (ATP) and L-methionine to interact with SAMe synthase (methionine adenosyltransferase) isolated and purified from microorganisms and a chemical synthesis method.

In the enzymatic synthesis method, SAMe is enzymatically synthesized by allowing substrates: adenosine 5'-triphosphate (ATP) and L-methionine to interact with SAMe synthase (methionine adenosyltransferase) isolated and purified from microorganisms. This method has an advantage that SAMe is accumulated in large quantities and not required to be extracted from microorganism cells, as compared with the fermentation method. However, this method has various problems including the complex preparation of the enzymes, the low activity of obtained enzymes, the necessity of removing interfering substances, such as ATPase, and the extremely high cost of ATP as a substrate, and therefore cannot necessarily be a practical method.

In addition, the recent progress of genetic engineering has led these enzymes to be prepared more conveniently by using cloned SAMe synthase genes so as to solve the problems involved in the preparation of enzymes. However, high-cost ATP still needs to be used as a substrate, and other practical problems have not been solved.

Furthermore, SAMe is thermolabile and easily degradable even at normal temperature, this presenting a major obstacle to its application to a medicine and a health food. To eliminate this problem, numerous attempts have been made to improve the storage stability. For example, a method is commonly used in which SAMe composition obtained by the above-mentioned production method is purified through chromatography or the like, and then converted into a salt of sulfuric acid, p-toluenesulfonic acid, or butanedisulfonic acid to stabilize SAMe, or in which the purified SAMe is added with an additive to provide a stabilized SAMe composition. These methods require great time and expense and therefore have extremely difficulty in producing and providing important SAMe inexpensively as a therapeutic agent and a health food.

Recently, studies have been made on SAMe-containing microorganisms (for example, see Non-patent Document 1) and SAMe-containing microorganism extracts by using orally available microorganisms having an ability to produce SAMe more conveniently and more inexpensively with fewer steps of purification (for example, see Patent Documents 1-4 and Non-Patent Document 2). At the present time, however, SAMe-containing microorganism extracts involve a problem of lower storage stability than purified SAMe and SAMe compositions.

PRIOR ART

Patent Documents

Patent document 1: JP 2005-229812A
Patent document 2: JP 2008-012464A
Patent document 3: WO 2009/081833
Patent document 4: JP 4479932B2
Patent document 5: WO 2011/1260303

Non-Patent Documents

Non Patent Document 1: Schlenk F., DePalma R. E., J. Biol. Chem. 1037-1050 (1957)
Non-Patent Document 2: Biochemica et Biophysica Acta, 1573, 105-108, (2002)

DISCLOSURE OF THE INVENTION

An objective of the present invention is to provide a composition containing a high concentration of SAMe and exhibiting excellent storage stability, a molded article formed by using the composition, and a process to conveniently and inexpensively produce the composition.

To solve the above-mentioned problems, the inventors made a great effort to study a composition containing a high concentration of SAMe and exhibiting long preservability with stable condition. As a result, the present inventors have found that the SAMe-containing dry yeast composition containing SAMe-containing yeast cells and a specific thickener has excellent storage stability. Based on this finding, the inventors have applied for a patent (see Patent Document 5).

However, a composition containing an SAMe-containing extract extracted from SAMe-containing yeast cells has not been studied.

Then, the inventors made a great effort to study a composition being formed by using an SAMe-containing extract, containing a high concentration of SAMe, and exhibiting long preservability under stable condition and also to study a method of economically producing the composition. As a result, the inventors have found that the following items of the invention can solve the above-mentioned problems. Based on this finding, the inventors have achieved the present invention.

[1] A composition includes S-adenosyl-L-methionine; and at least one kind of additive selected from carboxymethylcellulose, hydroxypropylcellulose, soybean polysaccharide, casein sodium, and zein, in which S-adenosyl-L-methionine is extracted from an S-adenosyl-L-methionine-containing cell obtained by culturing a microorganism having an ability to produce SAMe, and the content of the additive in the composition falls within the range of 0.05 to 15 times by mass of S-adenosyl-L-methionine in the composition.

[2] The composition according to [1], in which the microorganism is a microorganism belonging to genus *Saccharomyces*.

[3] The composition according to [2], in which the microorganism belonging to genus *Saccharomyces* is *Saccharomyces cerevisiae*.

[4] The composition according to any one of [1]-[3], in which the composition is solid.

[5] A molded article formed by using the composition according to [4].

[6] A method of producing a composition including S-adenosyl-L-methionine; and at least one kind of additive selected from carboxymethylcellulose, hydroxypropylcellulose, soybean polysaccharide, casein sodium, and zein, includes: mixing the additive with an S-adenosyl-L-methionine-containing extract extracted from a S-adenosyl-L-methionine-containing cell obtained by culturing a microorganism having an ability to produce SAMe, the content of the additive in the composition falling within the range of 0.05 to 15 times by mass of S-adenosyl-L-methionine in the S-adenosyl-L-methionine-containing extract; and drying the obtained mixture.

Effects of the Invention

The present invention can provide a composition containing a high concentration of SAMe and having excellent storage stability, a molded article formed by using the composition, and a method of economically producing the composition.

The SAMe-containing composition obtained by the present invention also has excellent bioabsorbability.

MODE FOR CARRYING OUT THE INVENTION

The composition of the present invention includes SAMe; and at least one kind of additive selected from carboxymethylcellulose, hydroxypropylcellulose, soybean polysaccharide, casein sodium, and zein, in which S-adenosyl-L-methionine is extracted from an S-adenosyl-L-methionine-containing cell obtained by culturing a microorganism having an ability to produce SAMe, and the content of the additive in the composition falls within the range of 0.05 to 15 times by mass of S-adenosyl-L-methionine in the composition.

The present invention will be explained below in detail.

The composition of the present invention containing a high concentration of SAMe and having excellent storage stability contains SAMe extracted from an SAMe-containing microorganism obtained by culturing a microorganism; and a specific additive.

The composition containing SAMe is widely used as a health food and the like, because the SAMe-containing composition contains a high proportion of useful components, such as 5'-nucleotide, free amino acid, glutathione with antioxidative effect helpful for improving liver function, and β-glucan and dietary fiber with the effect of improving immunity and regulating the functions of the intestines.

The type of microorganisms used in the present invention is not limited as long as the microorganisms are orally available and have SAMe-producing ability, which includes, for example, microorganisms belonging to genus *Saccharomyces, Candida, Pichia, Mucor, Rhizopus, Brevibacterium, Corynebacterium, Esherichia*, and *Streptomyces*. Among these, microorganisms belonging to genus *Saccharomyces* are preferable; *Saccharomyces cerevisiae* is more preferable, in particular.

The carbon source to be used for culturing the microorganisms mentioned above is not particularly limited as long as assimilated by the microorganisms. Examples of the carbon source include carbohydrate such as glucose, saccharose, starch, blackstrap molasses, alcohol such as ethanol, and organic acid such as acetic acid. The nitrogen source is also not particularly limited as long as assimilated by the microorganisms to be used. Examples of the nitrogen source include an inorganic nitrogen-containing compound, such as ammonia, nitric acid, and urea and a substance containing an organic nitrogen-containing compound, such as microorganism extract and malt extract. As an inorganic salt, a salt of phosphoric acid or a salt of potassium; sodium, magnesium, calcium, iron, zinc, manganese, cobalt, copper, or molybdenum is used. Furthermore, methionine, adenine, and adenosyl ribonucleoside that form the skeletal framework of SAMe can be added for culture.

The culture temperature may be 20 to 35° C. and the pH of the culture solution may be pH 4 to 7, although depending upon the type of microorganism to be used.

In order to increase the SAMe content in the microorganism cells, the microorganisms are preferably cultured aerobically. The type of culture tank is not limited as long as it can be ventilated and stirred if necessary and, for example, a mechanical stirring culture tank, an air-lift culture tank, a bubble column culture tank, and the like are usable.

The medium ingredients, such as carbon source, nitrogen source, various inorganic salts, various additives, and the like, are continuously or intermittently supplied together or individually. For example, the substrate, such as saccharose and ethanol, may be supplied to the fermenter as a mixture with other medium ingredients, or may be supplied to the fermenter independently from other medium ingredients.

The pH of the culture solution is controlled by an acid or alkali solution. Examples of the alkali include ammonia and urea which are also used as the nitrogen source and nonnitrogen base, such as sodium hydroxide and potassium hydroxide. Examples of the acid include an inorganic acid, such as phosphoric acid, sulfuric acid, and nitric acid, and an organic acid. The pH of the culture solution can be controlled also by using an inorganic salt, such as salt of phosphoric acid, potassium salt, sodium salt, and salt of nitric acid.

The culture is carried out under the conditions described above. The culture solution is withdrawn from the culture tank when a desired amount of SAMe is accumulated in the microorganism cells and then the microorganism cells are separated. The separation method is not limited as long as the microorganism cells can be efficiently separated and cleaned, with a counterflow yeast separator or an ultrafiltration system utilizing a separation membrane being preferred.

Then, SAMe is extracted from the separated microorganism cells. After extracted, the extract containing SAMe is mixed with an additive to obtain a liquid composition.

The process of obtaining an extract containing SAMe includes adding proteolytic enzyme, cell-wall digesting enzyme, or the like to a separated microorganism cell concentrate; conducting self-digestion using enzyme in microorganisms; conducting high-pressure grinding such as high-pressure dispersion; adding a mineral acid or an organic acid; or conducting heat-treatment.

The extract containing SAMe contains less solid content than microorganism cells containing SAMe, which is easily dispersed and dissolved in water, can therefore easily be added in foods, seasonings, and the like. The SAMe component can be concentrated.

The additive used in the present invention is at least one kind selected from carboxymethylcellulose, hydroxypropylcellulose, soybean polysaccharide, casein sodium, and zein. These additives can be used alone or in combination with two or more kinds. Among these, carboxymethylcellulose, hydroxypropylcellulose, and soybean polysaccharide are more preferable.

Soybean polysaccharide is a water-soluble polysaccharide based on hemicellulose, which is a polysaccharide composed of sugar such as galactose, arabinose, galacturonic acid, xylose, fucose, and rhamnose. Specifically, the product commercially available from FREUND (registered trade name: "hemilose") can preferably be used. Zein is a protein derived from corns. As zein, the hydrolysate or the sodium or potassium salts of this protein may be used. In the present invention, the use of a specific additive improves the storage stability of SAMe in the composition and the bioabsorbability of SAMe. The additive used in the present invention is used widely for foods, cosmetics, and medicines, so that it can be safely applied. As the additive, an appropriately synthesized compound or a commercially available product may be used.

The amount of the additive is required to fall within the range of 0.05 to 15, preferably 0.1 to 13.5, more preferably 0.15 to 13.5 times by mass of SAMe in the SAMe-containing extract before drying. The amount less than 0.05 times results in insufficient storage stability of SAMe in the composition. The amount more than 15 times produces no additional effect and shows a tendency to decrease the storage stability of SAMe in the composition depending upon the amount of use.

The mixing time of the SAMe-containing extract and the additive preferably falls within the range of from 1 min to 24 h. The mixing time less than 1 min results in insufficient storage stability of SAMe in the composition. The mixing time more than 24 h produces no additional effect and has the potential to decrease the SAMe content in the composition. This increases the storage stability and the bioabsorbability of SAMe in the composition during the mixing, improves the yield in the drying process of the below-mentioned composition, and masks odor peculiar to the composition containing SAMe.

After an additive is added and mixed, water is evaporated from the liquid composition by drying to produce an SAMe-containing dry composition in solid state. The drying process includes spray drying with a spray dryer and freeze drying.

The spray drying is preferably carried out at an inlet temperature of 210° C. or less and an exit temperature of 110° C. or less. The freeze drying is preferably carried out at a final shelf temperature of 30° C. or less. The dry composition of the present invention preferably has a water content of 5.0% by mass or less, preferably 3.0% by mass or less, more preferably 1.0% by mass or less from the viewpoint of storage stability.

The content of the additive in the composition falls within the range of 0.05 to 15, preferably 0.1 to 13.5, more preferably 0.15 to 13.5 times by mass of SAMe in the composition. The content less than 0.05 times results in insufficient storage stability of SAMe in the composition. The content more than 15 times shows a tendency to decrease the storage stability of SAMe in the composition depending upon the amount of use.

The content of SAMe in the composition is preferably 1% by mass or more, more preferably 3% by mass or more, further more 8% by mass or more based on the dry mass of the composition.

The obtained dry composition is solid, which can easily be molded. The molded article formed by using this dry SAMe-containing composition is used for various applications. For example, the dry SAMe-containing composition may be crushed into powder. After another physiological component or another additive, such as an excipient, is added to the powdery SAMe-containing composition, if needed, the resultant mixture including the SAMe-containing composition may be compressed and tabletted into a tablet composition. In addition, the surface of the tablet composition may be coated. Alternatively, the powdery dry SAMe-containing composition may be granulated, or the powdered or granulated dry SAMe-containing composition may be encapsulated.

EXAMPLES

The present invention will be explained below in more detail with reference to examples and comparative examples. However, it should be noted that the scope of the invention is not limited thereto.

Examples 1-1 to 1-3

(a) Culture of Microorganism Cells

According to the above-mentioned well-known culture method, *Saccharomyces cerevisiae* IFO2346 belonging to genus *Saccharomyces* was inoculated onto an L-methionine-containing medium (Shiozaki S., et al., J. Biotechnology, 4, 345-354 (1986)). The inoculated microorganism was aerobically cultured for six days at a culture temperature of 27 to 29° C. under stirring while introducing air. As a result, 18 L of a microorganism culture solution with a microorganism cell concentration of 3.5% by mass and an SAMe content of 205 mg/g.

(b) Collection of Microorganism Cells

The obtained 18 L of microorganism culture solution was centrifuged by a continuous rotary type centrifuge (Hitachi HIMAC CENTRIFUGE CR10B2) to obtain 3.4 kg of a liquid microorganism cell concentrate with a microorganism concentration of 18% by mass on dry basis.

(c) Extraction of Extract Containing SAMe from Microorganism Cell Concentrate

50% by mass of sulfuric acid is added to 3.4 kg of the above-mentioned microorganism cell concentrate to adjust the pH to 3.5. The microorganism cell concentrate was stirred while being heated at 50° C. for 30 min, transferred to a centrifuging tube, and subjected to cooling centrifugal separation with a centrifuge (Hitachi HIMAC CENTRIFUGE CR10B2). The supernatant was collected as the SAMe-containing extract.

(d) Addition of Additive to SAMe-Containing Extract

Hydroxypropylcellulose (hereinafter referred to as HPC) (available from Wako Pure Chemical Industries, Ltd.) was added in the above-mentioned SAMe-containing extracts, respectively in an amount of 0.19, 1.92, and 13.46 times by mass of SAMe in the respective SAMe-containing extracts before drying as shown in Table 1. Each of the mixtures was stirred at room temperature for 30 min to obtain a liquid SAMe-containing composition with HPC added.

(e) Preparation of Dry Composition Containing SAMe and Additive

The liquid SAMe-containing composition with HPC added was poured into a stainless tray of a freeze dryer (available from ULVAC, Inc.), frozen at −50° C., and then freeze-dried for 36 h at a final shelf temperature of 25° C. The obtained dry composition (solid) was crushed into powdery composition containing SAMe and HPC.

The obtained dry composition was packed in a glass container, which was then sealed. Then, a storage stability test was carried out under accelerated condition of 40° C. and 75% RH. The result of the accelerated storage stability test at 40° C. and 75% RH are shown in Table 1. The SAMe residual rate was determined by a comparative determination using liquid chromatography on SAMe extracted from the dry composition by a well-known method using perchloric acid. The presence of odor after storage was organoleptically determined by five panelists.

The SAMe measurement by liquid chromatography in the present invention was made under the following conditions.
Analysis Conditions Used:
Column: COSMOSIL (product name), 4.6ϕ×100 mm, available from Nacalai Tesque, Inc.
Eluant: 0.2 M $KH_2PO_4$ aqueous solution/methanol=95/5 (mass ratio)
Flow rate: 0.7 mL/min
Detector: UV (260 nm)
SAMe retention time: about 150 s Comparative Example 1

A powdery dry composition containing SAMe and HPC was obtained in the same manner as in Examples 1-1 to 1-3 with being freeze-dried except for adding HPC in the SAMe-containing extract in an amount of 0.02 times by mass of SAMe in the SAMe-containing extract before drying. The SAMe content in the composition, the result of the storage stability test for the composition packed in a sealed glass container under accelerated conditions of 40° C. and 75% RH, and the result of the organoleptic test are shown in Table 1.

Example 1-4

In the SAMe-containing extract obtained in the same manner as in the procedures (a) to (c) of Examples 1-1 to 1-3, HPC was added in an amount of 0.19 times by mass of SAMe in the extract on the procedure (d) of Examples 1-1 to 1-3. The mixture was stirred at room temperature for 30 min to obtain a liquid SAMe-containing composition with HPC added.

The obtained liquid SAMe-containing composition with HPC added was subjected to spray drying at an inlet temperature of 135° C., an exit temperature of 80° C., and a liquid feeding rate of 1.2 g/min using a mini spray dryer B-290 with a two-fluid nozzle (available from Metrohm AG) as a microparticulation device to obtain a powdery dry composition containing SAMe and HPC. The SAMe content in the composition, the result of the storage stability test for the composition packed in a sealed glass container under accelerated conditions of 40° C. and 75% RH, and the result of the organoleptic test are shown in Table 2.

Example 2

A powdery dry composition containing SAMe and carboxymethylcellulose was obtained in the same manner as in Examples 1-1 to 1-3 with being freeze-dried except for adding carboxymethylcellulose as the additive in the SAMe-containing extract in an amount of 0.19 times by mass of SAMe in the SAMe-containing extract before drying. The SAMe content in the composition, the result of the storage stability test for the composition packed in a sealed glass container under accelerated conditions of 40° C. and 75% RH, and the result of the organoleptic test are shown in Table 1.

Examples 3-1 to 3-3

A powdery dry composition containing SAMe and soybean polysaccharide was obtained in the same manner as in Examples 1-1 to 1-3 with being freeze-dried except for adding soybean polysaccharide (product name: "hemilose," available from FREUND) as the additive in the SAMe-containing extract. The SAMe content in the composition, the result of the storage stability test for the composition packed in a sealed glass container under accelerated conditions of 40° C. and 75% RH, and the result of the organoleptic test are shown in Tables 1 and 2.

Comparative Example 2

A powdery dry composition containing SAMe and soybean polysaccharide was obtained in the same manner as in Examples 1-1 to 1-3 with being freeze-dried except for adding soybean polysaccharide (product name: "hemilose," available from FREUND) in the SAMe-containing extract in an amount of 0.02 times by mass of SAMe in the SAMe-containing extract before drying. The SAMe content in the composition, the result of the storage stability test for the composition packed in a sealed glass container under accelerated conditions of 40° C. and 75% RH, and the result of the organoleptic test are shown in Table 1.

Example 3-4

A powdery dry composition containing SAMe and soybean polysaccharide was obtained in the same manner as in Example 1-4 with being spray-dried except for adding soybean polysaccharide (product name: "hemilose," available from FREUND) as the additive in the SAMe-containing extract. The SAMe content in the composition, the result of the storage stability test for the composition packed in a sealed glass container under accelerated conditions of 40° C. and 75% RH, and the result of the organoleptic test are shown in Table 2.

Comparative Example 3-1

A powdery dry composition containing SAMe was obtained in the same manner as in Examples 1-1 to 1-3 with being freeze-dried except for adding no additives in the SAMe-containing extract. The SAMe content in the composition, the result of the storage stability test for the obtained composition packed in a sealed glass container under accelerated conditions of 40° C. and 75% RH, and the result of the organoleptic test are shown in Table 1.

Comparative Example 3-2

A powdery dry composition containing SAMe was obtained in the same manner as in Example 1-4 with being spray-dried except for adding no additives in the SAMe-containing extract. The SAMe content in the composition, the result of the storage stability test for the composition packed in a sealed glass container under accelerated conditions of 40° C. and 75% RH, and the result of the organoleptic test are shown in Table 2.

Comparative Examples 4 to 9

Powdery dry compositions containing SAMe and an additive were obtained in the same manner as in Examples 1-1 to 1-3 with being freeze-dried except for adding trehalose, citric acid, EDTA, DL-malic acid, galactose, and γ-cyclodextrin shown in Table 1 as the additive in the SAMe-containing extracts, respectively in an amount of 2.31 times by mass of SAMe in the respective SAMe-containing extracts before drying. The SAMe content in the composition, the result of the storage stability test for the composition packed in a sealed glass container under accelerated conditions of 40° C. and 75% RH, and the result of the organoleptic test are shown in Table 1.

Comparative Examples 10 to 13

Powdery dry composition containing SAMe and an additive was obtained in the same manner as in Examples 1-1 to 1-3 with being freeze-dried except for adding cellulose, hydroxypropylmethylcellulose, tamarind gum, and shellac shown in Table 1 as the additive in the SAMe-containing extracts, respectively in an amount of 0.19 times by mass of SAMe in the respective SAMe-containing extracts before drying. The SAMe content in the composition, the result of the storage stability test for the composition packed in a sealed glass container under accelerated conditions of 40° C. and 75% RH, and the result of the organoleptic test are shown in Table 1.

TABLE 1

| Examples | Additive | Mass ratio of additive to SAMe in SAMe-containing extract before drying | SAMe content in SAMe-containing composition at start of test (% by mass) | Storage stability test SAMe residual rate of SAMe-containing composition Elapsed days | | | Presence of odor after 60 days* |
|---|---|---|---|---|---|---|---|
| | | | | 30 days | 45 days | 60 days | |
| Comparative Example 3-1 | None | 0.00 | 10.5 | 1.9% | 0.0% | 0.0% | C |
| Comparative Example 4 | Trehalose | 2.31 | 10.3 | 47.2% | 18.3% | 0.0% | C |
| Comparative Example 5 | Citric acid | | 10.8 | 58.2% | 26.5% | 3.5% | C |
| Comparative Example 6 | EDTA | | 10.4 | 61.3% | 29.7% | 5.4% | C |
| Comparative Example 7 | DL-malic acid | | 10.7 | 49.7% | 21.6% | 2.3% | C |
| Comparative Example 8 | Galactose | | 10.5 | 42.1% | 14.1% | 0.0% | C |
| Comparative Example 9 | γ-Cyclodextrin | | 10.6 | 98.5% | 98.6% | 45.5% | B |
| Comparative Example 10 | Cellulose | 0.19 | 17.0 | 99.7% | 92.6% | 85.2% | A |
| Comparative Example 11 | Hydroxypropylmethylcellulose | | 16.5 | 99.7% | 87.5% | 70.3% | A |
| Comparative Example 12 | Tamarind gum | | 15.9 | 99.7% | 84.8% | 68.3% | A |
| Comparative Example 13 | Shellac | | 17.3 | 99.7% | 99.7% | 99.4% | A |
| Comparative Example 1 | Hydroxypropylcellulose | 0.02 | 12.0 | 30.7% | 12.1% | 0.0% | C |
| Example 1-1 | Hydroxypropylcellulose | 0.19 | 18.8 | 99.5% | 99.5% | 99.5% | A |
| Example 1-2 | Hydroxypropylcellulose | 1.92 | 15.9 | 99.7% | 99.7% | 99.6% | A |
| Example 1-3 | Hydroxypropylcellulose | 13.46 | 5.5 | 99.7% | 99.7% | 99.6% | A |
| Example 2 | Carboxymethylcellulose | 0.19 | 17.0 | 99.7% | 99.7% | 99.4% | A |
| Comparative Example 2 | Soybean polysaccharide | 0.02 | 11.8 | 98.7% | 63.4% | 28.7% | B |
| Example 3-1 | Soybean polysaccharide | 0.19 | 17.3 | 99.7% | 99.7% | 99.4% | A |
| Example 3-2 | Soybean polysaccharide | 1.92 | 12.4 | 99.6% | 99.6% | 99.6% | A |
| Example 3-3 | Soybean polysaccharide | 13.46 | 5.3 | 99.8% | 99.8% | 99.7% | A |

*Organoleptic test: C: strong offensive odor, B: slight offensive odor, and A: no odor

TABLE 2

| Examples | Additive | Mass ratio of additive to SAMe in SAMe-containing extract before drying | SAMe content in SAMe-containing composition at start of test (% by mass) | Storage stability test SAMe residual rate of SAMe-containing composition Elapsed days | | | Presence of odor after 60 days* |
|---|---|---|---|---|---|---|---|
| | | | | 30 days | 45 days | 60 days | |
| Comparative Example 3-2 | None | 0.00 | 10.5 | 1.9% | 0.0% | 0.0% | C |
| Example 1-1 | Hydroxypropylcellulose | 0.19 | 18.8 | 99.5% | 99.5% | 99.5% | A |
| Example 3-1 | Soybean polysaccharide | 0.19 | 17.3 | 99.7% | 99.7% | 99.4% | A |
| Example 1-4 | Hydroxypropylcellulose | 0.19 | 18.1 | 99.5% | 99.5% | 99.5% | A |
| Example 3-4 | Soybean polysaccharide | 0.19 | 16.9 | 99.7% | 99.7% | 99.4% | A |

*Organoleptic test: C: strong offensive odor, B: slight offensive odor, and A: no odor Examples 4-1 to 4-3

A powdery dry composition containing SAMe and casein sodium was obtained in the same manner as in Examples 1-1 to 1-3 with being freeze-dried except for adding casein sodium as the additive in the SAMe-containing extract. The SAMe content in the composition, the result of the storage stability test for the obtained composition packed in a sealed glass container under accelerated conditions of 40° C. and 75% RH, and the result of the organoleptic test are shown in Tables 3 and 4.

Comparative Example 14

A powdery dry composition containing SAMe and casein sodium was obtained in the same manner as in Examples 1-1 to 1-3 with being freeze-dried except for adding casein sodium in the SAMe-containing extract in an amount of 0.02 times by mass in SAMe in the SAMe-containing extract before drying. The SAMe content in the composition, the result of the storage stability test for the composition packed in a sealed glass container under accelerated conditions of 40° C. and 75% RH, and the result of the organoleptic test are shown in Table 3.

Example 4-4

A powdery dry composition containing SAMe and casein sodium was obtained in the same manner as in Example 1-4 with being spray-dried except for adding casein sodium as the additive in the SAMe-containing extract. The SAMe content in the composition, the result of the storage stability test for the composition packed in a sealed glass container under accelerated conditions of 40° C. and 75% RH, and the result of the organoleptic test are shown in Table 4.

Examples 5-1 to 5-3

A powdery dry composition containing SAMe and zein was obtained in the same manner as in Examples 1-1 to 1-3 with being freeze-dried except for adding microcrystalline zein (product name: KOBAYASHI ZEIN DP, available from KOBAYASHI PERFUMERY CO., LTD) as the additive in the SAMe-containing extract. The SAMe content in the composition, the result of the storage stability test for the obtained composition packed in a sealed glass container under accelerated conditions of 40° C. and 75% RH, and the result of the organoleptic test are shown in Tables 3 and 4.

Comparative Example 15

A powdery dry composition containing SAMe and zein was obtained in the same manner as in Examples 1-1 to 1-3 with being freeze-dried except for adding microcrystal line zein (product name: KOBAYASHI ZEIN DP, available from KOBAYASHI PERFUMERY CO., LTD) in the SAMe-containing extract in an amount of 0.02 times by mass in SAMe in the SAMe-containing extract before drying. The SAMe content in the composition, the result of the storage stability test for the composition packed in a sealed glass container under accelerated conditions of 40° C. and 75% RH, and the result of the organoleptic test are shown in Table 3.

Example 5-4

A powdery dry composition containing SAMe and zein was obtained in the same manner as in Example 1-4 with being spray-dried except for adding microcrystalline zein (product name: KOBAYASHI ZEIN DP, available from KOBAYASHI PERFUMERY CO., LTD) as the additive in the SAMe-containing extract. The SAMe content in the composition, the result of the storage stability test for the composition packed in a sealed glass container under accelerated conditions of 40° C. and 75% RH, and the result of the organoleptic test are shown in Table 4.

Comparative Examples 16 to 19

A powdery dry composition containing SAMe and an additive was obtained in the same manner as in Examples 1-1 to 1-3 with being freeze-dried except for adding casein, gelatin, soy protein, and pea protein shown in Table 3 as the additive in the SAMe-containing extracts, respectively in an amount of 2.31 times by mass of SAMe in the respective SAMe-containing extracts before drying. The SAMe content in the composition, the result of the storage stability test for the composition packed in a sealed glass container under accelerated conditions of 40° C. and 75% RH, and the result of the organoleptic test are shown in Table 3.

TABLE 3

| Examples | Additive | Mass ratio of additive to SAMe in SAMe-containing extract before drying | SAMe content in SAMe-containing composition at start of test (% by mass) | Storage stability test SAMe residual rate of SAMe-containing composition Elapsed days 30 days | 45 days | 60 days | Presence of odor after 60 days* |
|---|---|---|---|---|---|---|---|
| Comparative Example 3-1 | None | 0.00 | 10.5% | 1.9% | 0.0% | 0.0% | C |
| Comparative Example 16 | Casein | 2.31 | 10.1% | 78.3% | 34.2% | 2.1% | C |
| Comparative Example 17 | Gelatin | | 10.2% | 78.7% | 35.1% | 2.4% | C |
| Comparative Example 18 | Soy protein | | 10.0% | 47.4% | 22.5% | 0.0% | C |
| Comparative Example 19 | Pea protein | | 10.4% | 48.5% | 23.7% | 0.0% | C |
| Comparative Example 14 | Casein sodium | 0.02 | 13.7% | 41.3% | 17.3% | 1.0% | C |
| Example 4-1 | Casein sodium | 0.19 | 17.1% | 99.6% | 99.6% | 99.6% | A |
| Example 4-2 | Casein sodium | 1.92 | 12.6% | 99.8% | 99.8% | 99.7% | A |
| Example 4-3 | Casein sodium | 13.46 | 5.7% | 99.8% | 99.8% | 99.8% | A |
| Comparative Example 15 | Zein | 0.02 | 13.2% | 99.6% | 99.6% | 82.6% | B |
| Example 5-1 | Zein | 0.19 | 17.8% | 99.8% | 99.8% | 99.7% | A |
| Example 5-2 | Zein | 1.92 | 12.3% | 99.8% | 99.8% | 99.7% | A |
| Example 5-3 | Zein | 13.46 | 5.6% | 99.8% | 99.8% | 99.8% | A |

*Organoleptic test: C: strong offensive odor, B: slight offensive odor, and A: no odor

TABLE 4

| Examples | Additive | Mass ratio of additive to SAMe in SAMe-containing extract before drying | SAMe content in SAMe-containing composition at start of test (% by mass) | Storage stability test SAMe residual rate of SAMe-containing composition Elapsed days 30 days | 45 days | 60 days | Presence of odor after 60 days* |
|---|---|---|---|---|---|---|---|
| Comparative Example 3-2 | None | 0.00 | 10.5% | 1.9% | 0.0% | 0.0% | C |
| Example 4-1 | Casein sodium | 0.19 | 17.1% | 99.6% | 99.6% | 99.6% | A |
| Example 5-1 | Zein | | 17.8% | 99.8% | 99.8% | 99.7% | A |
| Example 4-4 | Casein sodium | 0.19 | 16.6% | 99.5% | 99.4% | 99.4% | A |
| Example 5-4 | Zein | | 17.2% | 99.6% | 99.6% | 99.4% | A |

*Organoleptic test: C: strong offensive odor, B: slight offensive odor, and A: no odor Bioabsorbability Test The powdery dry compositions containing SAMe and an additive obtained in Examples 1-1, 2, 3-1, 4-1, and 5-1 and Comparative Example 13 and the powdery dry composition containing SAMe obtained in Comparative Example 3-1 were tested for the bioabsorbability by using SD rats (eight-week-old male rats, number of rats n=3 for each group) in the same manner as described in the literature (J of Chromatography B, 863, 94-100(2008)).

The powdery dry composition was dispersed in distilled water and orally administered to the rats in a dose of 300 mg/kg of rat on the basis of SAMe. Blood was taken from the rats after 0.5, 1, 2, 3 and 5 h of the oral administration and then promptly centrifuged to separate plasma components. Then, an SAMe component extract was obtained by using perchloric acid and analyzed by LC-MS-MS (Liquid chromatography coupled with mass spectrometry) method.

As a result of the bioabsorbability test, the concentration of SAMe in plasma was highest after two hours of the oral administration. The result of the bioabsorbability test after one hour and two hours of the oral administration of each powdery dry composition is shown in Table 5.

TABLE 5

| Examples | Additive | Mass ratio of additive to SAMe in SAMe-containing extract before drying | SAMe content in SAMe-containing composition at start of test (% by mass) | Concentration of SAMe in plasma (μg/ml) | |
|---|---|---|---|---|---|
| | | | | One hour after oral administration | Two hours after oral administration |
| Comparative Example 3-1 | None | 0.00 | 10.5 | 0.97 | 1.08 |
| Comparative Example 13 | Shellac | 0.19 | 17.3 | 0.82 | 0.97 |
| Example 1-1 | Hydroxypropylcellulose | 0.19 | 18.8 | 1.18 | 1.34 |
| Example 2 | Carboxymethylcellulose | | 17.0 | 1.19 | 1.37 |
| Example 3-1 | Soybean polysaccharide | | 17.3 | 1.22 | 1.41 |
| Example 4-1 | Casein sodium | | 17.1% | 1.18 | 1.36 |
| Example 5-1 | Zein | | 17.8% | 1.19 | 1.39 |

Table 5 shows that the SAMe-containing composition with an additive added, which belongs to the present invention, improves its bioabsorbability more than SAMe-containing compositions with no additives added. Table 5 also shows that the SAMe-containing composition with shellac added has lower bioabsorbability than SAMe-containing compositions with no additives added.

The analyzer and the conditions used in the bioabsorbability tests are as follows.

LC-MS-MS Method
  LC-MS-MS system: Accela, LTQ orbitrap Discovery available from Thermo Fisher Scientific, Inc.
HPLC Condition
  Column: Intersil ODS-3 (4.6 mm×150 mm) available from GL Sciences, Inc
  Flow rate: 0.5 mL/min
  Column oven: 40° C.
  Detector: UV (260 nm)
  SAMe retention time: about 145 s
  Injection rate: 10 μL
  Eluant: 2 mmol/L aqueous solution of L-heptafluorobutyric acid:acetonitrile=30:70
MS Condition
  Ion Source: ESI
  Ion Polarity Mode: Positive
  Scan Mode Type: FT full mass
  Resolution: 30000
  Mass Range: m/z 360-410

INDUSTRIAL APPLICABILITY

The composition of the present invention has excellent storage stability of SAMe effectively used as a medicine, an agricultural chemical, and a physiologically active substance for health foods. It is hence possible to supply a market with the composition of the present invention as a composition with excellent bioabsorbability. The production method of the present invention is useful as a method of conveniently and inexpensively producing a composition containing a high concentration of S-adenosyl-L-methionine and having excellent storage stability and bioabsorbability.

What is claimed is:

1. A composition comprising, in admixture:
    a microorganism cell extract comprising S-adenosyl-L-methionine; and
    at least one additive selected from the group consisting of soybean polysaccharide, casein sodium, and zein,
    wherein:
    the microorganism cell extract comprising S-adenosyl-L-methionine is extracted from an S-adenosyl-L-methionine-containing cell obtained by culturing a microorganism having an ability to produce S-adenosl-L-methionine;
    a content of the S-adenosyl-L-methionine in the composition is in a range of 3% to 18.8% by mass, based on the dry mass of the composition;
    a content of the additive in the composition is in a range of 0.05 to 15 times by mass of the S-adenosyl-L-methionine in the composition; and
    the admixture of the microorganism cell extract comprising S-adenosyl-L-methionine and the at least one additive is produced by mixing the microorganism cell extract comprising S-adenosyl-L-methionine and the at least one additive.

2. The composition according to claim 1, wherein the composition is solid.

3. A molded article comprising the composition according to claim 2.

4. The composition according to claim 1, comprising soybean polysaccharide.

5. The composition according to claim 1, comprising casein sodium.

6. The composition according to claim 1, comprising zein.

7. The composition according to claim 1, wherein the microorganism belongs to the genus *Saccharomyces, Candida, Pichia, Mucor, Rhizopus, Brevibacterium, Corynebacterium, Esherichia,* or *Streptomyces*.

8. The composition according to claim 1, wherein the microorganism is *Saccharomyces cerevisiae*.

* * * * *